(12) United States Patent
Vannucchi et al.

(10) Patent No.: US 9,358,229 B2
(45) Date of Patent: Jun. 7, 2016

(54) JAK PI3K/MTOR COMBINATION THERAPY

(75) Inventors: Alessandro M. Vannucchi, Florence (IT); Costanza Bogani, Prato (IT); Niccolo Bartalucci, Florence (IT)

(73) Assignees: Novartis Pharma AG, Basel (CH); Incyte Corporation, Wilmington, DE (US)

( * ) Notice: Subject to any disclaimer, the term of this patent is extended or adjusted under 35 U.S.C. 154(b) by 0 days.

(21) Appl. No.: 13/571,525

(22) Filed: Aug. 10, 2012

(65) Prior Publication Data

US 2013/0040973 A1   Feb. 14, 2013

Related U.S. Application Data

(60) Provisional application No. 61/522,001, filed on Aug. 10, 2011.

(51) Int. Cl.
*A61K 31/519* (2006.01)
*A61K 31/4745* (2006.01)

(52) U.S. Cl.
CPC ........... *A61K 31/4745* (2013.01); *A61K 31/519* (2013.01)

(58) Field of Classification Search
CPC ................ A61K 31/4745; A61K 31/519
See application file for complete search history.

(56) References Cited

U.S. PATENT DOCUMENTS

| | | | |
|---|---|---|---|
| 5,521,184 A | 5/1996 | Zimmermann | |
| 6,335,342 B1 | 1/2002 | Longo et al. | |
| 6,486,322 B1 | 11/2002 | Longo et al. | |
| 6,579,882 B2 | 6/2003 | Stewart et al. | |
| 6,635,762 B1 | 10/2003 | Blumenkopf et al. | |
| 6,852,727 B2 | 2/2005 | Goulet et al. | |
| 7,005,436 B2 | 2/2006 | Lloyd et al. | |
| 7,335,667 B2 | 2/2008 | Rodgers et al. | |
| 7,598,257 B2 | 10/2009 | Rodgers et al. | |
| 8,053,433 B2 | 11/2011 | Rodgers et al. | |
| 8,420,629 B2 | 4/2013 | Rodgers et al. | |
| 8,445,488 B2 | 5/2013 | Rodgers et al. | |
| 8,530,485 B2 | 9/2013 | Rodgers et al. | |
| 8,563,541 B2 | 10/2013 | Arvanitis et al. | |
| 8,604,043 B2 | 12/2013 | Li et al. | |
| 2003/0144309 A1 | 7/2003 | Choon-Moon | |
| 2003/0165576 A1 | 9/2003 | Fujii et al. | |
| 2004/0009983 A1 | 1/2004 | Cox et al. | |
| 2004/0029857 A1 | 2/2004 | Hale et al. | |
| 2004/0198737 A1 | 10/2004 | Cox et al. | |
| 2005/0153989 A1 | 7/2005 | Grotzfeld et al. | |
| 2006/0004010 A1 | 1/2006 | Habashita et al. | |
| 2006/0106020 A1 | 5/2006 | Rodgers et al. | |
| 2006/0183761 A1 | 8/2006 | Ledeboer et al. | |
| 2006/0183906 A1 | 8/2006 | Rodgers et al. | |
| 2007/0135461 A1 | 6/2007 | Rodgers et al. | |
| 2007/0135466 A1 | 6/2007 | Ledeboer et al. | |
| 2007/0149506 A1 | 6/2007 | Arvanitis et al. | |
| 2007/0208053 A1 | 9/2007 | Arnold et al. | |
| 2008/0188500 A1 | 8/2008 | Arvanitis et al. | |
| 2008/0207584 A1 | 8/2008 | Habashita et al. | |
| 2008/0312258 A1 | 12/2008 | Rodgers et al. | |
| 2008/0312259 A1 | 12/2008 | Rodgers et al. | |
| 2009/0018156 A1 | 1/2009 | Tang et al. | |
| 2009/0088445 A1 | 4/2009 | Ledeboer et al. | |
| 2009/0181959 A1 | 7/2009 | Rodgers et al. | |
| 2009/0197869 A1 | 8/2009 | Arvanitis et al. | |
| 2009/0215766 A1 | 8/2009 | Rodgers et al. | |
| 2009/0233903 A1 | 9/2009 | Rodgers et al. | |
| 2009/0318405 A1 | 12/2009 | Li et al. | |
| 2010/0113416 A1 | 5/2010 | Friedman et al. | |
| 2010/0190981 A1 | 7/2010 | Zhou et al. | |
| 2010/0298334 A1 | 11/2010 | Rodgers et al. | |
| 2011/0059951 A1 | 3/2011 | Rodgers et al. | |
| 2011/0082159 A1 | 4/2011 | Rodgers et al. | |
| 2011/0086810 A1 | 4/2011 | Rodgers et al. | |
| 2011/0086835 A1 | 4/2011 | Rodgers et al. | |
| 2011/0207754 A1 | 8/2011 | Li et al. | |
| 2011/0224157 A1 | 9/2011 | Rodgers et al. | |
| 2011/0224190 A1 | 9/2011 | Huang et al. | |
| 2011/0263005 A1 | 10/2011 | Chang et al. | |
| 2011/0288107 A1 | 11/2011 | Parikh et al. | |
| 2012/0149681 A1 | 6/2012 | Rodgers et al. | |
| 2012/0149682 A1 | 6/2012 | Rodgers et al. | |
| 2012/0214825 A1 | 8/2012 | Vannucchi et al. | |
| 2012/0301464 A1 | 11/2012 | Friedman et al. | |
| 2013/0018034 A1 | 1/2013 | Yao et al. | |
| 2013/0045963 A1 | 2/2013 | Rodgers et al. | |
| 2013/0060026 A1 | 3/2013 | Zhou et al. | |
| 2013/0137681 A1 | 5/2013 | Rodgers et al. | |
| 2013/0225556 A1 | 8/2013 | Rodgers et al. | |
| 2013/0253190 A1 | 9/2013 | Zhou et al. | |
| 2013/0253191 A1 | 9/2013 | Zhou et al. | |
| 2013/0253193 A1 | 9/2013 | Zhou et al. | |

FOREIGN PATENT DOCUMENTS

| | | |
|---|---|---|
| DE | 30 36 390 | 5/1982 |
| WO | 97/02262 A1 | 1/1997 |
| WO | 99/62908 A2 | 12/1999 |
| WO | 99/65908 A1 | 12/1999 |
| WO | 99/65909 A1 | 12/1999 |

(Continued)

OTHER PUBLICATIONS

Fiskus et al. Journal of the Amenica Chemical Society; 52nd Annual Meeting of the American Society of Hematology, Orlando, FL Dec. 4-7, 2010. https://ash.confex.com/ash/2010/webprogram/Paper31710.html.*

(Continued)

*Primary Examiner* — Savitha Rao
*Assistant Examiner* — Angela Brown-Pettigrew
(74) *Attorney, Agent, or Firm* — Lathrop & Gage LLP; Brian C. Trinque

(57) ABSTRACT

Provided herein is a combination therapy comprising a JAK kinase inhibitor and a dual PI3K/mTOR inhibitor, as well as methods of treating various cancers through the use of such a combination therapy.

9 Claims, No Drawings

(56) References Cited

FOREIGN PATENT DOCUMENTS

| | | |
|---|---|---|
| WO | 00/09495 A2 | 2/2000 |
| WO | 00/53595 A1 | 9/2000 |
| WO | 01/14402 A1 | 3/2001 |
| WO | 01/42246 A2 | 6/2001 |
| WO | 01/64655 A1 | 9/2001 |
| WO | 01/81345 A1 | 11/2001 |
| WO | 02/00196 A2 | 1/2002 |
| WO | 02/00661 A1 | 1/2002 |
| WO | 02/055084 A1 | 7/2002 |
| WO | 02/060492 A1 | 8/2002 |
| WO | 02/096909 A1 | 12/2002 |
| WO | 03/011285 A1 | 2/2003 |
| WO | 03/024967 A2 | 3/2003 |
| WO | 03/037347 A1 | 5/2003 |
| WO | 03/048162 A1 | 6/2003 |
| WO | 03/099771 A2 | 12/2003 |
| WO | 2004/005281 A1 | 1/2004 |
| WO | 2004/041814 A1 | 5/2004 |
| WO | 2004/046120 A2 | 6/2004 |
| WO | 2004/047843 A1 | 6/2004 |
| WO | 2004/056786 A2 | 7/2004 |
| WO | 2004/072063 A1 | 8/2004 |
| WO | 2004/080980 A1 | 9/2004 |
| WO | 2004/099204 A1 | 11/2004 |
| WO | 2004/099205 A1 | 11/2004 |
| WO | 2005/013986 A1 | 2/2005 |
| WO | 2005/028444 A1 | 3/2005 |
| WO | 2005/051393 A1 | 6/2005 |
| WO | 2005/060972 A2 | 7/2005 |
| WO | 2005/095400 A1 | 10/2005 |
| WO | 2005/105146 A1 | 11/2005 |
| WO | 2005/105814 A1 | 11/2005 |
| WO | 2005/105988 A2 | 11/2005 |
| WO | 2005/110410 A2 | 11/2005 |
| WO | 2005/121130 A2 | 12/2005 |
| WO | 2006/013114 A1 | 2/2006 |
| WO | 2006/046023 A1 | 5/2006 |
| WO | 2006/046024 A1 | 5/2006 |
| WO | 2006/056399 A2 | 6/2006 |
| WO | 2006/069080 A2 | 6/2006 |
| WO | 2006/096270 A1 | 9/2006 |
| WO | 2006/122806 A2 | 11/2006 |
| WO | 2006/127587 A1 | 11/2006 |
| WO | 2006/129199 A1 | 12/2006 |
| WO | 2006/136823 A1 | 12/2006 |
| WO | 2007/002433 A1 | 1/2007 |
| WO | 2007/025090 A2 | 3/2007 |
| WO | 2007/041130 A2 | 4/2007 |
| WO | 2007/062459 A1 | 6/2007 |
| WO | 2007/070514 A1 | 6/2007 |
| WO | 2007/076423 A2 | 7/2007 |
| WO | 2007/077949 A1 | 7/2007 |
| WO | 2007/084557 A2 | 7/2007 |
| WO | 2007/117494 A1 | 10/2007 |
| WO | 2008/145688 A2 | 12/2008 |
| WO | 2008/157208 A2 | 12/2008 |
| WO | 2009/049028 A1 | 4/2009 |
| WO | 2009/064835 A1 | 5/2009 |
| WO | 2009/114512 A1 | 9/2009 |
| WO | 2010/081692 A1 | 7/2010 |
| WO | 2013/023119 A1 | 2/2013 |

OTHER PUBLICATIONS

Quintás-Cardama et al. Blood, Apr. 15, 2010, vol. 115, No. 15.*
Neidle's Cancer Drug Design and Discovery (Elsevier/Academic Press, 2008, pp. 427-431; cited in PTO-892.*
US Food and Drug Administration approved small molecule protein kinase inhibitors, http://www.brimr.org/PKI/PK1s.htm, accessed: Mar. 27, 2014.*
Tallarida et al (Chemofog: Cancer Chemotherapy-Induced Cognitive Deficits (2009).*
Anderson et al: Biochemical characterization of GSK1070916, a potent and selective inhibitor of Aurora B and Aurora C kinases with an extremely long residence time; Biochem J; vol. 420, pp. 259-265 (2009).
Baudouin: Flow Cytometry in Impression Cytology Specimens; Investigative Ophthalmology & Visual Science; vol. 38(7), pp. 1458-1464 (1997).
Bollrath et al: gp130-Mediated Stat3 Activation in Enterocytes Regulates Cell Survival and Cell-Cycle Progression during Colitis-Associated Tumorigenesis; Cancer Cell, vol. 15:91-102 (2009).
Bromberg et al: Inflammation and Cancer: IL-6 and STAT3 Complete the Link; Cancer Cell, vol. 15 (2), pp. 79-80 (2009).
Carey, Francis A. et al: Oxidations; Advanced Organic Chemistry; Fourth Edition, Kluwer Academic/Plenum Publishers, New York, Chpt. 12, pp. 747-757 (2001).
Gaertner, Van R., "Cyclization of 1-Alkylamino-3-halo-2-alkanols to 1-Alkyl-3-azetidinols," J. Org. Chem., vol. 32 (10):2972-2976 (1967).
Gooseman, Natalie E.J. et al., "The intramolecular beta-fluorine—ammonium interaction in 4- and 8-membered rings," Chem. Commun., vol. 30:3190-3192 (2006).
Hamze, Abdallah et al., "Synthesis of Various 3-Substituted 1,2,4-Oxadiazole-Containing Chiral b3- and a-Amino Acids from Fmoc-Protected Aspartic Acid," J. Org. Chem., vol. 68:7316-7321 (2003).
Hardwicke, Mary Ann et al., "GSK1070916, a potent Aurora B/C kinase inhibitor with broad antitumor activity in tissue culture cells and human tumor xenograft models," Mol. Cancer Ther., vol. 8(7):1808-1817 (2009).
Helal, Christopher J. et al., "Stereoselective Synthesis of cis-1,3-Disubstituted Cyclobutyl Kinase Inhibitors," Organic Letters, vol. 6(11):1853-1856 (2004).
Higuchi, T. et al., Pro-drugs as Novel Drug Delivery Systems, ACS Symposium Series: American Chemical Society, Washington, D.C., vol. 14 (1974), 240 pages.
International Preliminary Report on Patentability for Application No. PCT/US2008/066662, dated Dec. 17, 2009, 16 pages.
Lin, et al.; Enantioselective Synthesis of Janus Kinase Inhibitor INCB018424 via an Organocatalytic Aza-Michael Reaction; American Chemical Society, Org. Lett., vol. 11, No. 9, 2009, pp. 1999-2002.
Sawada, et al.; Increased Lipophilicity and Subsequent Cell Partitioning Decrease Passive Transcellular Diffusion of Novel, Highly Lipophilic Antioxidants; J Pharmacology and Experimental Therapeutics; 1999; vol. 288, No. 3, pp. 1317-1326.
Abstract of Chilean patent application No. 3496-06, published in Official Gazette of the Republic of Chile, Jun. 1, 2007, 1 page.
Letter from Chilean foreign counsel reporting the publication of the abstract of Chilean patent application No. 3496-06, Jun. 5, 2007, 1 page.
Schindler, et al.; Cytokines and STAT Signaling; Advances in Pharmacology: Hormones and Signaling; 2000;47:113-74.
Roudebush, Roger E.; Pharmacologic manipulation of a four day murine delayed type hypersensitivity model; Agents Actions.; Jan. 1993; 38(1-2):116-21.
26th Annual JPMorgan Healthcare Conference presentation dated Jan. 8, 2008, 28 pages.
Bell, Malcolm, and Zalay, Andrew, "Synthesis of Substituted 3-Amino[6, 5-b] triazmmdoles." Journal of Heterocyclic Chemistry, 12(5):1001-1004, Oct. 1975.
Gorr, M.E. et al., "Clinical Resistance to STI-571 Cancer Therapy Caused by BCR-ABL Gene Mutation or Amplification." Science, 293:876, 2001.
Blume-Jensen et al: Oncogenic kinase signalling; Nature; 2001, vol. 411, pp. 355-365.
Bolen: Nonreceptor tyrosine protein kinases; Oncogene; 1993, vol. 8(8), pp. 2025-2031.
Borie et al: Combined Use of the JAK3 Inhibitor CP-690,550 with Mycophenolate Mofetil to Prevent Kidney Allograft Rejection in Nonhuman Primates; Transplantation; 2005, vol. 80, No. 12, pp. 1756-1764.
Boudny et al: JAK/STAT signaling pathways and cancer; J Neoplasm; 2002, vol. 49, pp. 349-355.

(56) References Cited

OTHER PUBLICATIONS

Bowman et al: STATs in oncogenesis; Oncogene, 2000, vol. 19, pp. 2474-2488.
Burger et al: Gp130 and ras mediated signaling in human plasma cell line INA-6: a cytokine-regulated tumor model for plasmacytoma; Hematol J; 2001, vol. 2, pp. 42-53.
Candotti et al: Molecular aspects of primary immunodeficiencies: lessons from cytokine and other signaling pathways; J Clin Invest; 2002, vol. 109(10), pp. 1261-1269.
Candotti et al: Structural and functional basis for JAK3-deficient severe combined immunodeficiency; Blood; 1997, vol. 90(10): 3996-4003.
Cetkovic-Cvrlje et al: Targeting JAK3 with JANEX-1 for prevention of autoimmune type 1 diabetes in NOD mice; Clin Immunol; 2003, vol. 106(3): 213-25.
Chalandon et al: Targeting mutated protein tyrosine kinases and their signaling pathways in hematologic malignancies; Hematologica; 2005, vol. 90, pp. 949-968.
Changelian et al: Prevention of Organ Allograft Rejection by a Specific Janus Kinase 3 Inhibitor; Science; 2003, vol. 302, pp. 875-878.
Chen et al: Stat3 Activation in Human Endometrial and Cervical Cancer; British Journal of Cancer, 2007, vol. 96, pp. 591-599.
Conklyn, M. et al: The JAK3 inhibitor CP-690550 Selectively reduces NK and CD8+ cell numbers cynomolgus monkey blood following chronic oral dosing; Journal of Leukocyte Biology, 2004, vol. 76, pp. 1248-1255.
Gotlieb, Alice, Presentation at the 2008 American Academy of Dermatology, 66th Annual Meeting, San Antonio, TX, Feb. 1, 2008, Symposium-303, 12 pages.
Daniels et al., "Imatinib mesylate inhibits the profibrogenic activity of TGF-13 and prevents bleomycinmediated lung fibrosis." J. Clin. Invest., 114(9):1308-1316, Nov. 2004.
Deuse et al: Novel Immunosuppression: R348, a JAK3- and Syk-Inhibitor Attenuates Acute Cardiac Allograft Rejection; Transplantation; 2008, vol. 85(6), pp. 885-892.
Doleschall G., and Lempert, K., "Thermal and Acid Catalysed Degradations of 3-Alykylthio-6,7-Dihydro-[I.2.4] Triazino[1.6-c]Quinazolin-5-Ium- I-Olates." Tetrahedron, 30:3997-4012, 1974.
De Vos, J., M. Jourdan, et al., "JAK2 tyrosine kinase inhibitor tyrphostin AG490 downregulates the mitogen-activated protein kinase (MAPK) and signal transducer and activator of transcription (STAT) pathways and induces apoptosis in myeloma cells." Br J Haematol, 2000, vol. 109(4): 823-8.
Dudley et al: A VEGF/JAK2/STAT5 axis may partially mediate endothelial cell tolerance to hypoxia; Biochem. J.; 2005, vol. 390, pp. 427-436.
Quesada et al: One-pot conversion of activated alcohols into 1,1-dibromoalkenes and terminal alkynes using tandem oxidation processes with manganese dioxide; Tetrahedron; 2006, vol. 62, pp. 6673-6680.
Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007, 1 page.
Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009, 1 page.
Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, Poster 285, 1 page.
Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007, 1 page.
Fridman, J. et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark, 1 page.
Fiskus et al: Synergistic Activity of Combinations of JAK2 Kinase Inhibitor with PI3K/mTOR, MEK or PIM Kinase Inhibitor Against Human Myeloproliferative Neoplasm Cells Expressing JAK2V617F; J. Amer Chem Soc; 52nd Annual Meeting of the American-Sociaety of Hematology; Orlando, FL, USA; Dec. 4-7, 2010, Abstract, ACS Publications, US, 1 page.
Grabbe, et al: Immunoregulatory mechanisms involved in elicitation of allergic contact hypersensitivity; Immunol Today; 1998, vol. 19(1), pp. 37-44.
Ishizaki et al: Pharmacological Properties of Y-27632, a Specific Inhibitor of Rho-Associated Kinases; Molecular Pharmacology; 2000, vol. 57, pp. 976-983.
Itagaki et al: Expedient Synthesis of Potent Cannabinoid Receptor Agonist (-)-CP55,940; Organic Letters; 2005, vol. 7(19), pp. 4181-4183.
James et al: A unique clonal JAK2 mutation leading to constitutive signalling causes polycythaemia vera; Nature; 2005, vol. 434, pp. 1144-1148.
Zou et al: Signaling Pathways Activated by Oncogenic Forms of Abl Tyrosine Kinase; Journal of Biological Chemistry; 1999, vol. 274(26), pp. 18141-18144.
Kawamura et al: Molecular cloning of L-JAK, a Janus family protein-tyrosine kinase expressed in natural killer cells and activated leukocytes; Proc Natl Acad Sci USA, 1994, vol. 91(14), pp. 6374-6378.
Kharas et al: ABL Oncogenes and Phosphoinositide 3-Kinase: Mechanism of Activation and Downstream Effectors; Cancer Res; 2005, vol. 65(6), pp. 2047-2053.
Kruh et al: The complete coding sequence of arg defines the Abelson subfamily of cytoplasmic tyrosine kinases; Proc. Natl. Acad. Sci., 1990, vol. 87, pp. 5802-5806.
Kubinyi: Qsar: Hansch Analysis and Related Approaches; Methods and Principles in Medicinal Chemistry; eds, Manhold et al., Weinhein, NY, 1993, 42 pages.
Kudelacz et al: The JAK-3 inhibitor CP-690550 is a potent anti-inflammatory agent in a murine model of pulmonary eosinophilia; European Journal of Pharmacology; 2008, vol. 582, pp. 154-161.
Levine, et al: Activating mutation in the tyrosine kinase JAK2 in polycythemia vera, essential thrombocythemia, and myeloid metaplasia with myelofibrosis; Cancer Cell, 2005, vol. 7, pp. 387-397.
Madhusudan: Tyrosine kinase inhibitors in cancer therapy; Clin Biochem; 2004, vol. 37(7), pp. 618-635.
Manning et al: tHE pROTEIN kINASE cOMPLEMENT of The Human Genome; Science; 2002, vol. 298, pp. 1912-1934.
Wu et al: One-Pot Two-Step Microwave-Assisted Reaction in Constructing 4,5-disubstituted Pyrazolopyrimidines; Organic Letters, 2003, vol. 5(20), pp. 3587-3590.
Milici, A.J., et al: Cartilage preservation by inhibition of Janus kinase 3 in two rodent models of rheumatoic arthritis; Arthritis Research & Therapy 2008, 10:R14 (http://arthritis-research.com/content/10/1/R14), 9 pages.
Nakagawara, Akira, "Trk receptor tyrosine kinases: A bridge between cancer and neural development." Cancer Letters, 2001, vol. 169, pp. 107-114.
Neubauer et al: JAK2 Deficiency Defines an Essential Developmental Checkpoint in Definitive Hematopoiesis; Cell; 1998, vol. 93(3), pp. 397-409.
Nishio et al: Tyrosine kinase-dependent modulation by interferon-alpha of the ATP-sensitive K+ current in rabbit ventricular myocytes; FEBS Letters; 1999, vol. 445, pp. 87-91.
Palmer, Amparo, and Klein, Rudiger, "Multiple roles of ephrins in morphogenesis, neuronal networking, and brain function." Genes & Dev., 17:1429-1450, 2003.
Patani, G.A. et al: Bioisosterism: A Rational Approach in Drug Design; Chem. Rev. 1996, vol. 96, pp. 3147-3176.
Parganas et al: Jak2 Is Essential for Signaling through a Variety of Cytokine Receptors; Cell; 1998, vol. 93(3), pp. 385-395.

(56) References Cited

OTHER PUBLICATIONS

Park et al: Homogeneous Proximity Tyrosine Kinase Assays: Scintillation Proximity Assay versus Homogeneous Time-Resolved Fluorescence; Analytical Biochemistry; 1999, vol. 269, pp. 94-104.
Pernis et al: JAK-STAT signaling in asthma; J Clin Invest; 2002, vol. 109(10), pp. 1279-1283.
International Search Report and Written Opinion for PCT/US2006/047369, dated Apr. 24, 2007, 16 pages.
Press Release dated Sep. 18, 2008: Incyte's Topical JAK Inhibitor Demonstrates Positive Proof-of-Concept Results in Patients with Mild to Moderate Psoriasis, 4 pages.
Punwani, et al. "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008, poster presentation, 15 pages.
Remington's Pharmaceutical Sciences, 17th ed., Mack Publishing Company, Easton, Pa., 1985, p. 1418.
Rodig et al: "Disruption of the Jakl gene demonstrates obligatory and nonredundant roles of the Jaks in cytokine-induced biologic responses." Cell, 1998, vol. 93(3), pp. 373-383.
Rousvoal et al: Janus kinase 3 inhibition with CP-690,550 prevents allograft vasculopathy; Transpl Int; 2006,vol. 12, pp. 1014-1021.
Saemann, M. D., C. Diakos, et al. (2003). "Prevention of CD40-triggered dendritic cell maturation and induction of T-cell hyporeactivity by targeting of Janus kinase 3." Am J Transplant, vol. 3(11), pp. 1341-1349.
Scott, M. J., C. J. Godshall, et al. (2002). "Jaks, STATs, Cytokines, and Sepsis." Clin Diagn Lab Immunol 9(6): 1153-9.
Seto, Y., H. Nakajima, et al. (2003). "Enhanced Th2 cell-mediated allergic inflammation in Tyk2-deficient mice." J Immunol 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.
Sriram et al: Induction of gp130-related Cytokines and Activation of JAK2/STAT3 Pathway in Astrocytes Precedes Up-regulation of Glial Fibrillary Acidic Protein in the 1-Methyl-4phenyl1-1,2,3,6-tetrahydropyridine Model of neurodegeneration; J. Biol. Chem; 2004, vol. 279(19), pp. 19936-19947.
Staerk et al: JAK1 and Tyk2 Activation by the Homologous Polycythemia Vera JAK2 V617F Mutation, Cross-Talk With IGF1 Receptor; JBC; 2005, vol. 280, pp. 41893-41899.
Tefferi, A. et al.; The Clinical Phenotype of Myelofibrosis Encompasses a Chronic Inflammatory State that is Favorably Altered by INCB018424, A Selective Inhibitor of JAK1/2; Poster #2804 at The American Society of Hematology Annual Meeting (ASH), Dec. 7, 2008, 2 pages.
Ortmann, R. A., T. Cheng, et al. Janus kinases and signal transducers and activators of transcription: their roles in cytokine signaling, development and immunoregulation; Arthritis Res; 2000, vol. 2(1), pp. 16-32.
Takemoto, S., J. C. Mulloy, et al. (1997). "Proliferation of adult T cell leukemia/lymphoma cells is associated with the constitutive activation of JAK/STAT proteins." Proc Natl Acad Sci U S A 94(25): 13897-902.
Thompson et al: Photochemical Preparation of a Pyridone Containing Tetracycle: a Jak Protein Kinase Inhibitor; Bioorganic & Medicinal Chemistry Letters, vol. 12 (2002), pp. 1219-1223.
Verstovsek, S., et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007.
Verstovsek, S., et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark; 2 pages.
Verstovsek, S. et al.; INCB18424 Discussion, American Society of Hematology, Dec. 10, 2007; presentation, 16 pages.
Verstovsek, S., et al.; Characterization of JAK2 V617F Allele Burden in Advanced Myelofibrosis (MF) Patients: No Change in V617F:WT JAK2 Ratio in Patients with High Allele Burdens Despite Profound Clinical Improvement Following Treatment with the JAK Inhibitor INCB018242, Poster #2802 at the American Society of Hematoloogy Annual Meeting (ASH), Dec. 7, 2008, 2 pages.
Verstovsek, S. et al.; The JAK Inhibitor, INCB018242, Demonstrates Durable and Marked Clinical Responses in Primary Myelofibrosis (PMF) and Post-Polycythemia/Essential Thrombocythemia Myelofibrosis (Post PV/ET-MF), Poster #1762, 2 pages.
Verbeeck, et al.; Biowaiver Monographs for Immediate Release Solid Oral Dosage Forms Based on Biopharmaceutics Classification System (BCS) Literature Data: Chloroquine Phosphate, Chloroquine Sulfate, and Chloroquine Hydrochloride; J Pharma Sci; 2005, 94:7, 1389-1395.
Seefeld, et al., Discovery of 5-pyrrolopyridinyl-2-thiophenecarboxamides as potent AKT kinase inhibitors; Bioorganic & Medicinal Chemistry Letters 19 20092244-2248.
Chloroquine phosphate, material data safety sheet 9MSDS), downloaded Jun. 15, 2010 <http://www.sciencelab.com/xMSDS-Chloroquine_phosphate-9923444>; pp. 1-6.
Chloroquine phosphate, material data safety sheet 9MSDS), downloaded Jun. 15, 2010 <http://www.lookchem.com/Chloroquine/>; pp. 1-6.
Berge et al: Pharmaceutical Salts; J. of Pharmaceutical Sciences; 1977, vol. 66(1), pp. 1-19.
International Search Report and Written Opinion, PCT/US2012/05052, dated Jan. 2, 2013, 11 pages.

* cited by examiner

JAK PI3K/MTOR COMBINATION THERAPY

PRIORITY BENEFIT

This application claims the benefit of U.S. Provisional Application No. 61/522,001 filed on Aug. 10, 2011, the contents of which are hereby incorporated herein in its entirety. The contents of any patents, patent applications, and references cited throughout this specification are hereby incorporated by reference in their entireties.

BACKGROUND

Cancer is a major cause of death in the United States. Although "cancer" is used to describe many different types of cancer, e.g., breast, prostate, lung, colon, and pancreatic, each type of cancer differs both at the phenotypic level and the genetic level. The unregulated growth characteristic of cancer occurs when the expression of one or more genes becomes disregulated due to mutations, and cell growth can no longer be controlled.

Myeloproliferative neoplasms (MPNs) are a group of cancers that cause an overproduction of blood cells (platelets, white blood cells and red blood cells) in the bone marrow. MPNs include polycythemia vera (PV), primary or essential thrombocythemia (ET), primary or idiopathic myelofibrosis, chronic myelogenous (myelocytic) leukemia (CML), chronic neutrophilic leukemia (CNL), juvenile myelomonocytic leukemia (JML) and chronic eosinophilic leukemia (CEL)/hyper eosinophilic syndrome (HES). These disorders are grouped together because they share some or all of the following features: involvement of a multipotent hematopoietic progenitor cell, dominance of the transformed clone over the non-transformed hematopoietic progenitor cells, overproduction of one or more hematopoietic lineages in the absence of a definable stimulus, growth factor-independent colony formation in vitro, marrow hypercellularity, megakaryocyte hyperplasia and dysplasia, abnormalities predominantly involving chromosomes 1, 8, 9, 13, and 20, thrombotic and hemorrhagic diatheses, exuberant extramedullary hematopoiesis, and spontaneous transformation to acute leukemia or development of marrow fibrosis but at a low rate, as compared to the rate in CML. The incidence of MPNs varies widely, ranging from approximately 3 per 100,000 individuals older than 60 years annually for CML to 0.13 per 100,000 children from birth to 14 years annually for JML (Vardiman J W et al., Blood 100 (7): 2292-302, 2002).

Accordingly, there remains a need for new treatments of MPNs, as well as other cancers such as solid tumors.

SUMMARY OF THE INVENTION

Provided herein is a combination therapy comprising a compound of the formula I:

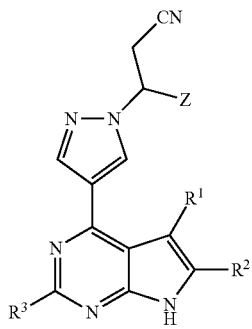

(I)

including stereoisomers, tautomers, racemates, solvates, metabolites, and pharmaceutically acceptable salts thereof, and a compound of the formula II:

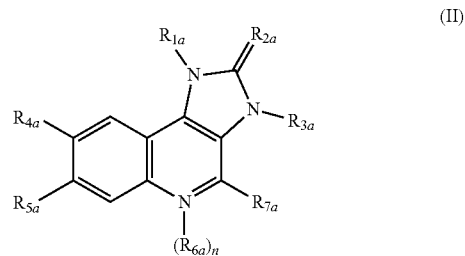

(II)

including tautomers, hydrates, solvates, and pharmaceutically acceptable salts thereof.

In a particular embodiment, the compound of formula I is (3R)-3-cyclopentyl-3-[4-(7H-pyrrolo[2,3-d]pyrimidin-4-yl)-1H-pyrazol-1-yl]propanenitrile, or a pharmaceutically acceptable salt thereof. In another particular embodiment, the compound of formula II is 2-methyl-2-[4-(3-methyl-2-oxo-8-quinolin-3-yl-2,3-dihydro-imidazo[4,5-c]quinolin-1-yl)-phenyl]-propionitrile.

The combination therapy is useful for the treatment of a variety of cancers, including MPNs and solid tumors. The combination therapy is also useful for the treatment of any number of JAK-associated diseases, as well as diseases that can be treated through the dual inhibition of PI3K/mTOR.

In one embodiment, provided herein is a combination therapy comprising a JAK inhibitor of the formula I, as well as a dual PI3K/mTOR inhibitor of the formula II. In one embodiment, the JAK inhibitor is (3R)-3-cyclopentyl-3-[4-(7H-pyrrolo[2,3-d]pyrimidin-4-yl)-1H-pyrazol-1-yl]propanenitrile, and the dual PI3K/mTOR inhibitor is 2-methyl-2-[4-(3-methyl-2-oxo-8-quinolin-3-yl-2,3-dihydro-imidazo[4,5-c]quinolin-1-yl)-phenyl]-propionitrile. As such, in one aspect, provided herein is a pharmaceutical composition comprising (3R)-3-cyclopentyl-3-[4-(7H-pyrrolo[2,3-d]pyrimidin-4-yl)-1H-pyrazol-1-yl]propanenitrile or salts thereof and 2-methyl-2-[4-(3-methyl-2-oxo-8-quinolin-3-yl-2,3-dihydro-imidazo[4,5-c]quinolin-1-yl)-phenyl]-propionitrile, or pharmaceutically acceptable salts thereof and a pharmaceutically acceptable carrier.

In another embodiment of the combination therapy, the JAK inhibitor is (3R)-3-cyclopentyl-3-[4-(7H-pyrrolo[2,3-d]pyrimidin-4-yl)-1H-pyrazol-1-yl]propanenitrile phosphoric acid salt. Accordingly, in one embodiment provided herein is a combination therapy comprising the JAK inhibitor, (3R)-3-cyclopentyl-3-[4-(7H-pyrrolo[2,3-d]pyrimidin-4-yl)-1H-pyrazol-1-yl]propanenitrile phosphoric acid salt and the dual PI3K/mTOR inhibitor, 2-methyl-2-[4-(3-methyl-2-oxo-8-quinolin-3-yl-2,3-dihydro-imidazo[4,5-c]quinolin-1-yl)-phenyl]-propionitrile or a pharmaceutically acceptable salt thereof.

In one embodiment of the combination therapy, the compound of formula I and the compound of formula II can be in a single formulation or unit dosage form. The single formulation or unit dose form can further comprise a pharmaceutically acceptable carrier.

In another aspect, provided herein is a method of treating cancer in a subject in need thereof comprising administering to the subject an effective amount of a compound of formula I and a compound of formula II. The cancer to be treated can be a myeloproliferative neoplasm. Examples of myeloproliferative neoplasms include those selected from the group consisting of chronic myeloid leukemia (CML), polycythemia vera (PV), essential thrombocythemia (ET), primary or idiopathic myelofibrosis (PMF), chronic neutrophilic leukemia, chronic eosinophilic leukemia, chronic myelomonocytic leukemia, juvenile myelomonocytic leukemia, hypereosinophilic syndrome, systemic mastocytosis, and atypical chronic myelogenous leukemia.

In one embodiment of the cancer treatment, the cancer is a solid tumor. Examples of solid tumors to be treated include tumors of the brain, kidney, liver, adrenal gland, bladder, breast, stomach, gastric area, ovaries, colon, rectum, prostate, pancreas, lung, vagina, thyroid, neck or head.

In another embodiment, the cancer to be treated is Waldenström's macroglobulinemia.

In another embodiment of the methods provided herein, the subject is human.

When used in these methods, the compound of formula I and the compound of formula II can be in a single formulation or unit dosage form. In other embodiments of the methods, the compound of formula I and the compound of formula II are in separate formulations or unit dosage forms. Alternatively, the treatment comprises administering the compound of formula I and the compound of formula II at substantially the same time. In still another embodiment, treatment can comprise administering compound of formula I and the compound of formula II at different times. In another embodiment, the compound of formula I is administered to the subject, followed by administration of the compound of formula II. Alternatively, the compound of formula II is administered to the subject, followed by administration of the compound of formula I.

In another embodiment, the compound of formula I and/or compound of formula II is administered at dosages that would not be effective when one or both of the compound of formula I and the compound of formula II is administered alone, but which amounts are effective in combination.

DETAILED DESCRIPTION

It has been discovered that administering a combination of a JAK kinase inhibitor (e.g., a compound of formula I) and a dual PI3K/mTOR inhibitor (e.g., a compound of formula II) provides surprising, synergistic effects for treating cancer, e.g., myeloproliferative neoplasms (MPNs) and solid tumors, in a subject. Such an approach, combination or co-administration of the two types of agents, can be useful for treating individuals suffering from cancer who do not respond to or are resistant to currently-available therapies. The combination therapy provided herein is also useful for improving the efficacy and/or reducing the side effects of currently-available cancer therapies for individuals who do respond to such therapies.

Certain terms used herein are described below. Compounds of the present invention are described using standard nomenclature. Unless defined otherwise, all technical and scientific terms used herein have the same meaning as is commonly understood by one of skill in the art to which this invention belongs.

JAK Inhibitor/PI3K/mTOR Combination

Provided herein is a combination of therapeutic agents and administration methods for the combination of agents to treat cancer, e.g., MPNs and solid tumors. As used herein, a "combination of agents" and similar terms refer to a combination of two types of agents: (1) a JAK inhibitor of the formula I, and (2) a dual PI3K/mTOR inhibitor of the formula II.

The JAK family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs (Scott, M. J., C. J. Godshall, et al. (2002) Clin. Diagn. Lab Immunol. 9(6): 1153-9).

As used herein, a "JAK inhibitor" refers to a compound or a ligand that inhibits at least one activity of a JAK kinase. A "JAK inhibitor" can also be a "JAK1/JAK2 inhibitor." In certain embodiments, the JAK inhibitor induces a JAK-inhibited state. An example of a JAK inhibitor is a compound of formula I.

The compounds of formula I are defined as follows:

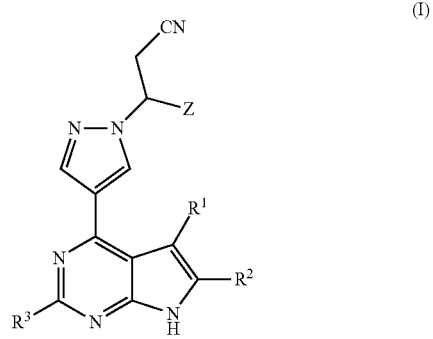

(I)

including stereoisomers, tautomers, racemates, solvates, metabolites, and pharmaceutically acceptable salts thereof, wherein $R^1$, $R^2$ and $R^3$ are independently selected from H, halo, and $C_{1-4}$ alkyl; and Z is $C_{3-6}$ cycloalkyl (e.g., cyclopentyl).

Examples of compounds of formula I include the compounds described in U.S. patent application Ser. No. 12/137, 892, U.S. patent application Ser. No. 12/687,623 and U.S. Pat. No. 7,598,257, all of which are incorporated herein by reference in their entireties.

In a particular embodiment, the compound of formula I is 3-cyclopentyl-3-[4-(7H-pyrrolo[2,3-d]pyrimidin-4-yl)-1H-pyrazol-1-yl]propanenitrile or a pharmaceutically acceptable salt thereof. In another embodiment, the compound of formula I is (3R)-3-cyclopentyl-3-[4-(7H-pyrrolo[2,3-d]pyrimidin-4-yl)-1H-pyrazol-1-yl]propanenitrile or a pharmaceutically acceptable salt thereof. In still another embodiment, the compound of formula I is (3S)-3-cyclopentyl-3-[4-(7H-pyrrolo[2,3-d]pyrimidin-4-yl)-1H-pyrazol-1-yl]propanenitrile or a pharmaceutically acceptable salt thereof. The synthesis of these compounds are described in, for example, U.S. Pat. No. 7,598,257, and in U.S. patent application Ser. No. 12/687, 623, both of which are incorporated herein by reference in its entirety.

In another embodiment, the compound of formula I is (3R)-3-cyclopentyl-3-[4-(7H-pyrrolo[2,3-d]pyrimidin-4-yl)-1H-pyrazol-1-yl]propanenitrile maleic acid salt. In still another embodiment, the compound of formula I is (3R)-3-cyclopentyl-3-[4-(7H-pyrrolo[2,3-d]pyrimidin-4-yl)-1H-pyrazol-1-yl]propanenitrile sulfuric acid salt. In yet another embodiment, the compound is of formula I is (3R)-3-cyclopentyl-3-[4-(7H-pyrrolo[2,3-d]pyrimidin-4-yl)-1H-pyrazol-1-yl]propanenitrile phosphoric acid salt. The synthesis of these compounds are described in, for example, U.S. patent application Ser. No. 12/137,892, which is incorporated herein by reference in its entirety.

Phosphatidylinositol (PI) is a phospholipid that is found in cell membranes. This phosphoholipid plays an important role also in intracellular signal transduction. Phosphatidylinositol-3 kinase (PI3K) has been identified as an enzyme that phosphorylates the 3-position of the inositol ring of phosphatidylinositol [D. Whitman et al., Nature, 332, 664 (1988)].

Mammalian Target of Rapamycin (mTOR), is a cell-signaling protein that regulates the response of tumor cells to nutrients and growth factors, as well as controlling tumor blood supply through effects on Vascular Endothelial Growth Factor, (VEGF) Inhibitors of mTOR starve cancer cells and shrink tumors by inhibiting the effect of mTOR, which is a downstream mediator of the PI3K/Akt pathway. The PI3K/Akt pathway is thought to be over-activated in numerous cancers and may account for the widespread response from various cancers to mTOR inhibitors. Over-activation of the PI3K/Akt kinase pathway is frequently associated with mutations in the PTEN gene, which is common in many cancers and may help predict what tumors will respond mTOR inhibitors.

The efficacy of a dual PI3K/mTOR inhibitor has been described, for example, in Mol. Cancer. Ther., 7(7): 1851-1863 (July 2008) and PNAS, 106(52): 22299-22304 (Dec. 29, 2009).

Compounds of formula II, having the structure provided below, are dual PI3K/mTOR inhibitors:

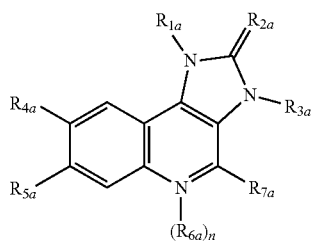

(II)

including tautomers, hydrates, solvates, and pharmaceutically acceptable salts thereof, wherein $R_{1a}$ is phenyl wherein said phenyl is substituted by one or two substituents independently selected from the group consisting of halogen; $C_{1-4}$ alkyl unsubstituted or substituted by halogen, cyano, imidazolyl or triazolyl; $C_{3-6}$ cycloalkyl; amino substituted by one or two substituents independently selected from the group consisting of $C_{1-4}$ alkyl, $C_{1-4}$ alkyl sulfonyl, and $C_{1-4}$ alkoxy; piperazinyl unsubstituted or substituted by one or two substituents independently selected from the group consisting of $C_{1-4}$ alkyl and $C_{1-4}$ alkyl sulfonyl; 2-oxo-pyrrolidinyl; imidazolyl; pyrazolyl; and triazolyl;

$R_{2a}$ is O or S;
$R_{3a}$ is $C_{1-4}$ alkyl;
$R_{4a}$ is pyridyl unsubstituted or substituted by halogen, cyano, $C_{1-4}$ alkyl, $C_{1-4}$ alkoxy or piperazinyl unsubstituted or substituted by $C_{1-4}$ alkyl; pyrimidinyl unsubstituted or substituted by $C_{1-4}$ alkyl; quinolinyl unsubstituted or substituted by halogen; or quinoxalinyl;
$R_{5a}$ is hydrogen or halogen;
n is 0 or 1, wherein if n=1, the N-atom bearing the radical $R_6$ has a positive charge;
$R_{6a}$ is oxido; and
$R_{7a}$ is hydrogen or amino.

In a particular embodiment, the compound of formula II is of the formula IIa:

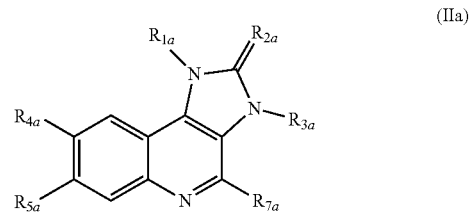

(IIa)

including tautomers, hydrates, solvates, and pharmaceutically acceptable salts thereof,
wherein
$R_{1a}$ is phenyl wherein said phenyl is substituted by one or two substituents independently selected from the group consisting of halogen; $C_{1-4}$ alkyl unsubstituted or substituted by halogen, cyano, imidazolyl or triazolyl; and piperazinyl unsubstituted or substituted by one or two substituents independently selected from the group consisting of $C_{1-4}$ alkyl and $C_{1-4}$ alkyl sulfonyl;
$R_{2a}$ is O;
$R_{3a}$ is $C_{1-4}$ alkyl;
$R_{4a}$ is quinolinyl unsubstituted or substituted by halogen;
$R_{5a}$ is hydrogen;
and
$R_{7a}$ is hydrogen.

In one embodiment, the compound of formula II has a structure including tautomers, hydrates, solvates, and pharmaceutically acceptable salts thereof,
wherein:
$R_{1a}$ is phenyl wherein said phenyl is substituted by $C_{1-4}$ alkyl unsubstituted or substituted by halogen, cyano, imidazolyl or triazolyl;
$R_{2a}$ is O;
$R_{3a}$ is $C_{1-4}$ alkyl;
$R_{4a}$ is quinolinyl unsubstituted or substituted by halogen;
$R_{5a}$ is hydrogen;
n is 0; and
$R_{7a}$ is hydrogen.

In another embodiment, the compound of formula II is 2-methyl-2-[4-(3-methyl-2-oxo-8-quinolin-3-yl-2,3-dihydro-imidazo[4,5-c]quinolin-1-yl)-phenyl]-propionitrile, and pharmaceutically acceptable salts thereof. In still another embodiment, the compound of Formula II is the monotosylate salt of 2-methyl-2-[4-(3-methyl-2-oxo-8-quinolin-3-yl-2,3-dihydro-imidazo[4,5-c]quinolin-1-yl)-phenyl]-propionitrile. These compounds, as well as other compounds of formula II, are described in WO/2006/122806, as well as WO/2008/103636, each of which are incorporated herein by reference in their entireties.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, 1 to 6 carbons, 1 to 4 carbons, or 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

As used herein, the term "cycloalkyl" refers to saturated or unsaturated monocyclic, bicyclic or tricyclic hydrocarbon groups of 3-12 carbon atoms, preferably 3-9, or 3-6 carbon atoms. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

The term "halogen" or "halo" refers to chloro, bromo, fluoro, and iodo groups.

The term "amino" as used herein unless otherwise specified, includes a moiety represented by the structure "—$NR_2$", and includes primary, secondary and tertiary amines optionally substituted by alkyl, alkoxy, aryl, heterocyclyl, alkyl sulfonyl and/or sulfonyl groups. For example, $R_2$ may represent two hydrogen atoms, two alkyl moieties, or one hydrogen and one alkyl moiety.

Agents may contain one or more asymmetric elements such as stereogenic centers or stereogenic axes, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms; all isomeric forms of the compounds are included in the present invention. In these situations, the single enantiomers (optically active forms) can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Unless otherwise specified, or clearly indicated by the text, reference to compounds useful in the combination therapy of the invention includes both the free base of the compounds, and all pharmaceutically acceptable salts of the compounds.

As used herein, the term "pharmaceutically acceptable salts" refers to the nontoxic acid or alkaline earth metal salts of the pyrimidine compounds of the invention. These salts can be prepared in situ during the final isolation and purification of the pyrimidine compounds, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-naphth-alenesulfonate, oxalate, pamoate, pectinate, persulfate, 3-phenylproionate, phosphate, picrate, pivalate, propionate, succinate, sulfate, tartrate, thiocyanate, p-toluenesulfonate, and undecanoate.

Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, hydrobromic acid, nitric acid, sulfuric acid and phosphoric acid and such organic acids as formic acid, acetic acid, trifluoroacetic acid, fumaric acid, tartaric acid, oxalic acid, maleic acid, methanesulfonic acid, succinic acid, malic acid, methanesulfonic acid, benzenesulfonic acid, and p-toluenesulfonic acid, citric acid, and acidic amino acids such as aspartic acid and glutamic acid.

Basic addition salts can be prepared in situ during the final isolation and purification of the pyrimidine compounds, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine, pyridine, picoline, triethanolamine and the like, and basic amino acids such as arginine, lysine and ornithine.

Provided herein is a combination therapy comprising a JAK inhibitor of the formula I and a PI3K/mTOR inhibitor of the formula II. Administration of the combination includes administration of the combination in a single formulation or unit dosage form, administration of the individual agents of the combination concurrently but separately, or administration of the individual agents of the combination sequentially by any suitable route. The dosage of the individual agents of the combination may require more frequent administration of one of the agent(s) as compared to the other agent(s) in the combination. Therefore, to permit appropriate dosing, packaged pharmaceutical products may contain one or more dosage forms that contain the combination of agents, and one or more dosage forms that contain one of the combinations of agents, but not the other agent(s) of the combination.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, or in separate containers (e.g., capsules) for each active ingredient. In addition, such administration also encompasses use of each type of therapeutic agent in a sequential manner, either at approximately the same time or at different times. In either case, the treatment regimen will provide beneficial effects of the drug combination in treating the conditions or disorders described herein The term "single formulation" as used herein refers to a single carrier or vehicle formulated to deliver effective amounts of both therapeutic agents to a patient. The single vehicle is designed to deliver an effective amount of each of the agents, along with any pharmaceutically acceptable carriers or excipients. In some embodiments, the vehicle is a tablet, capsule, pill, or a patch. In other embodiments, the vehicle is a solution or a suspension.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of at least one of the agents along with pharmaceutically acceptable carriers and excipients. In some embodiments, the unit dose is one or more tablets, capsules, pills, or patches administered to the patient at the same time.

The term "treat" is used herein to mean to relieve, reduce or alleviate, at least one symptom of a disease in a subject. Within the meaning of the present invention, the term "treat" also denotes, to arrest, delay the onset (i.e., the period prior to clinical manifestation of a disease or symptom of a disease) and/or reduce the risk of developing or worsening a symptom of a disease.

The term "subject" is intended to include animals. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer, e.g., myeloproliferative neoplasms or solid tumors.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

The combination of agents described herein display a synergistic effect. The term "synergistic effect" as used herein, refers to action of two agents such as, for example, a JAK inhibitor of the formula I and a PI3K/mTOR inhibitor of the formula II, producing an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., *Clin. Pharmacokinet.* 6: 429-453 (1981)), the equation of Loewe additivity (Loewe, S, and Muischnek, H., Arch. Exp. *Pathol. Pharmacol.* 114: 313-326 (1926)) and the median-effect equation (Chou, T. C. and Talalay, P., *Adv. Enzyme Regul.* 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

An "effective amount" of a combination of agents (i.e., a JAK inhibitor of the formula I and a PI3K/mTOR inhibitor of the formula II) is an amount sufficient to provide an observable improvement over the baseline clinically observable signs and symptoms of the depressive disorder treated with the combination.

An "oral dosage form" includes a unit dosage form prescribed or intended for oral administration.

Methods of Treatment Using a Combination of a Formula I JAK Inhibitor and a Formula II PI3K/mTOR Inhibitor Provided herein are methods of treating cancer, e.g., myeloproliferative neoplasms and solid tumors, using the combination therapy treatment described above.

As used herein, "cancer" refers to any disease that is caused by or results in inappropriately high levels of cell division, inappropriately low levels of apoptosis, or both. Examples of cancer include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic rnyelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors.

Furthermore, the combination therapy provided herein relates to a pharmaceutical composition for treatment of solid or liquid tumors in warm-blooded animals, including humans, comprising an antitumor-effective dose of compounds of the combination as described above.

The combination therapy provided herein can be used in the treatment of solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangio sarcoma, lymphangioendotheliosarcoma, synovioma, mesothelioma, Ewing's tumor, leiomyo sarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, crailiopharyngioma, ependymoma, pinealoma, hemangioblastoma, acoustic neuroma, oligodenroglioma, schwamioma, meningioma, melanoma, neuroblastoma, and retinoblastoma).

In a certain embodiment, the cancer that can be treated using the combination provided herein is a myeloproliferative disorder. Myeloproliferative disorders (MPDs), now commonly referred to as meyloproliferative neoplasms (MPNs), are in the class of haematological malignancies that are clonal disorders of hematopoietic progenitors. Tefferi, A. and Vardiman, J. W., Classification and diagnosis of myeloproliferative to neoplasms: The 2008 World Health Organization criteria and point-of-care diagnostic algorithms, *Leukemia*, September 2007, 22: 14-22, is hereby incorporated by reference. They are characterized by enhanced proliferation and survival of one or more mature myeloid lineage cell types. This category includes but is not limited to, chronic myeloid leukemia (CML), polycythemia vera (PV), essential thrombocythemia (ET), primary or idiopathic myelofibrosis (PMF), chronic neutrophilic leukemia, chronic eosinophilic leukemia, chronic myelomonocytic leukemia, juvenile myelomonocytic leukemia, hypereosinophilic syndrome, systemic mastocytosis, and atypical chronic myelogenous leukemia. Tefferi, A. and Gilliland, D. G., Oncogenes in myeloproliferative disorders, *Cell Cycle*. March 2007, 6(5): 550-566 is hereby fully incorporated by reference in its entirety for all purposes.

In another embodiment, the combination therapy provided herein is useful for the treatment of primary myelofibrosis, post-polycythemia vera myelofibrosis, post-essential thrombocythemia myelofibrosis, and secondary acute myelogenous leukemia.

In some embodiments, the subject to be treated (e.g., a human) is determined to be non-responsive or resistant to one or more therapies for myeloproliferative disorders.

In a particular embodiment, provided herein is a method of treating a myeloproliferative neoplasm in a subject in need thereof, comprising administering to the subject an effective amount of (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, and 2-methyl-2-[4-(3-methyl-2-oxo-8-quinolin-3-yl-2,3-dihydro-imidazo[4,5-c]quinolin-1-yl)-phenyl]-propionitrile, or a pharmaceutically acceptable salt thereof. When used in these methods, the compound of formula I and the compound of formula II can be in a single formulation or unit dosage form. In other embodiments of the methods, the compound of formula I and the compound of formula II are in separate formulations or unit dosage forms.

In a particular embodiment, provided herein is a method of treating a solid tumor in a subject in need thereof, comprising administering to the subject an effective amount of a composition comprising (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, and 2-methyl-2-[4-(3-methyl-2-oxo-8-quinolin-3-yl-2,3-dihydro-imidazo[4,5-c]quinolin-1-yl)-phenyl]-propionitrile, or a pharmaceutically acceptable salt thereof. When used in these methods, the compound of formula I and the compound of formula II can be in a single formulation or unit dosage form. In other embodiments of the methods, the compound of formula I and the compound of formula II are in separate formulations or unit dosage forms.

Furthermore, the invention relates to a method for the treatment of a proliferative disease which responds to an inhibition of lipid kinases and/or PI3-kinase-related protein kinases, in particular the PI3 kinase, and/or DNA protein kinase activity, which comprises administering a combination of a compound of formula I and a compound of formula II, in a quantity effective against the said disease, to a warm-blooded animal, in particular to humans, requiring such treatment.

Preferred diseases that respond to an inhibition of lipid kinases and/or PI3-kinase-related protein kinases are those proliferative diseases selected from a benign or malignant tumor, carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, lymphomas, a mammary carcinoma or a leukemia. Other diseases include Cowden syndrome, Lhermitte-Dudos disease and Bannayan-Zonana syndrome, or diseases in which the PI3K/PKB pathway is aberrantly activated.

In one embodiment, provided herein are methods of treating a JAK-associated disease or disorder in a subject (e.g., patient) by administering to the individual in need of such treatment a therapeutically effective amount or dose of a combination of the present invention or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, type I diabetes, lupus, psoriasis, inflammatory bowel disease, ulcerative colitis, Crohn's disease, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma etc.), hematological cancers (e.g., lymphoma, leukemia such as acute lymphoblastic leukemia, or multiple myeloma), and skin cancer such as cutaneous T-cell lymphoma (CTCL) and cutaneous B-cell lymphoma. Example cutaneous T-cell lymphomas include Sezary syndrome and mycosis fungoides.

JAK-associated diseases can further include those characterized by expression of a mutant JAK2 such as those having at least one mutation in the pseudo-kinase domain (e.g., JAK2V617F).

JAK-associated diseases can further include myeloproliferative disorders (MPDs) such as polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), systemic mast cell disease (SMCD), and the like.

Further JAK-associated diseases include inflammation and inflammatory diseases. Example inflammatory diseases include inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases.

The combination therapy described herein can further be used to treat ischemia reperfusion injuries or a disease or condition related to an inflammatory ischemic event such as stroke or cardiac arrest. The combination therapy described herein can further be used to treat anorexia, cachexia, or fatigue such as that resulting from or associated with cancer. The combination therapy described herein can further be used to treat restenosis, sclerodermitis, or fibrosis. The combination therapy described herein can further be used to treat conditions associated with hypoxia or astrogliosis such as, for example, diabetic retinopathy, cancer, or neurodegeneration. See, e.g., Dudley, A. C. et al. Biochem. J. 2005, 390(Pt 2):427-36 and Sriram, K. et al. J. Biol. Chem. 2004, 279(19): 19936-47. Epub 2004 Mar. 2.

Provided herein are methods of treating disease, e.g., a myeloproliferative disorder, by administering an effective amount of a compound of a dual action PI3K/mTOR inhibitor and a JAK inhibitor to an individual suffering from a disease. The amount of the combination of agents is effective to treat the disease. It is important to note the synergistic effects of the combination of agents: even though one or more of the agents administered alone at a particular dosage may not be effective, when administered in combination, at the same dosage of each agent, the treatment is effective. The doses of the one or more of the agents in the combination therefore can be less than the FDA approved doses of each agent.

The pharmaceutical compositions or combinations provided herein (i.e., a JAK inhibitor of the formula I and a dual PI3K/mTOR inhibitor of the formula II) can be tested in clinical studies. Suitable clinical studies may be, for example, open label, dose escalation studies in patients with proliferative diseases. Such studies prove in particular the synergism of the active ingredients of the combination of the invention. The beneficial effects on proliferative diseases may be determined directly through the results of these studies which are known as such to a person skilled in the art. Such studies may, in particular, be suitable to compare the effects of a monotherapy using the active ingredients and a combination of the invention. In one embodiment, the dose of a compound of formula I is escalated until the Maximum Tolerated Dosage is reached, and the compound of formula I is administered with a fixed dose. Alternatively, the compound of formula II may be administered in a fixed dose and the dose of the compound of formula I may be escalated. Each patient may receive doses of the compounds either daily or intermittently. The efficacy of the treatment may be determined in such studies, e.g., after 12, 18 or 24 weeks by evaluation of symptom scores every 6 weeks.

The administration of a pharmaceutical combination of the invention may result not only in a beneficial effect, e.g. a synergistic therapeutic effect, e.g. with regard to alleviating, delaying progression of or inhibiting the symptoms, but also in further surprising beneficial effects, e.g. fewer side-effects, an improved quality of life or a decreased morbidity, compared with a monotherapy applying only one of the pharmaceutically active ingredients used in the combination of the invention.

A further benefit may be that lower doses of the active ingredients of the combination of the invention may be used, for example, that the dosages need not only often be smaller but may also be applied less frequently, which may diminish the incidence or severity of side-effects. This is in accordance with the desires and requirements of the patients to be treated.

It is one objective of this invention to provide a pharmaceutical composition comprising a quantity, which may be jointly therapeutically effective at targeting or preventing cancer, e.g., a myeloproliferative disorder. In this composition, a compound of formula I and a compound of formula II may be administered together, one after the other or separately in one combined unit dosage form or in two separate unit dosage forms. The unit dosage form may also be a fixed combination.

The pharmaceutical compositions for separate administration of both compounds, or for the administration in a fixed combination, e.g. a single composition comprising both compounds according to the invention may be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g. as indicated above, or in combination with one or more pharmaceutically acceptable carriers or diluents, especially suitable for enteral or parenteral application.

Formulations

The drug combinations provided herein may be formulated by a variety of methods apparent to those of skill in the art of pharmaceutical formulation. The various release properties described above may be achieved in a variety of different ways. Suitable formulations include, for example, tablets, capsules, press coat formulations, and other easily administered formulations.

Suitable pharmaceutical formulations may contain, for example, from about 0.1% to about 99.9%, preferably from about 1% to about 60%, of the active ingredient(s). Pharmaceutical formulations for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount may be reached by administration of a plurality of dosage units.

The pharmaceutical compositions can contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, for example see International Patent Application No. WO 2002/000196.

Some examples of suitable excipients include lactose (e.g. lactose monohydrate), dextrose, sucrose, sorbitol, mannitol, starches (e.g. sodium starch glycolate), gum acacia, calcium phosphate, alginates, tragacanth, gelatin, calcium silicate, colloidal silicon dioxide, microcrystalline cellulose, polyvinylpyrrolidone (e.g. povidone), cellulose, water, syrup, methyl cellulose, and hydroxypropyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

In particular, a therapeutically effective amount of each of the combination partner of the combination of the invention may be administered simultaneously or sequentially and in any order, and the components may be administered separately or as a fixed combination. For example, the method of treating a disease according to the invention may comprise (i) administration of the first agent (a) in free or pharmaceutically acceptable salt form and (ii) administration of an agent (b) in free or pharmaceutically acceptable salt form, simultaneously or sequentially in any order, in jointly therapeutically effective amounts, preferably in synergistically effective amounts, e.g. in daily or intermittently dosages corresponding to the amounts described herein. The individual combination partners of the combination of the invention may be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of the combination partners employed in the combination of the invention may vary depending on the particular compound or pharmaceutical composition employed, the mode of administration, the condition being treated, the severity of the condition being treated. Thus, the dosage regimen of the combination of the invention is selected in accordance with a variety of factors including the route of administration and the renal and hepatic function of the patient. A clinician or physician of ordinary skill can readily determine and prescribe the effective amount of the single active ingredients required to alleviate, counter or arrest the progress of the condition.

Dosages

The optimal dose of the combination of agents for treatment of disease can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

The amount of combination of agents that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

The dosage form can be prepared by various conventional mixing, comminution and fabrication techniques readily apparent to those skilled in the chemistry of drug formulations.

The oral dosage form containing the combination of agents or individual agents of the combination of agents may be in the form of micro-tablets enclosed inside a capsule, e.g. a gelatin capsule. For this, a gelatin capsule as is employed in pharmaceutical formulations can be used, such as the hard gelatin capsule known as CAPSUGEL, available from Pfizer.

Many of the oral dosage forms useful herein contain the combination of agents or individual agents of the combination of agents in the form of particles. Such particles may be compressed into a tablet, present in a core element of a coated dosage form, such as a taste-masked dosage form, a press coated dosage form, or an enteric coated dosage form, or may be contained in a capsule, osmotic pump dosage form, or other dosage form.

In an embodiment, the drug compounds of the present invention (for example, a dual PI3K/mTOR inhibitor and a JAK inhibitor) are present in the combinations, dosage forms, pharmaceutical compositions and pharmaceutical formulations disclosed herein in a ratio in the ranges of, for example, approximately 100:1 to 1:100, 75:1 to 1:75, 50:1 to 1:50, 20:1 to 1 to 20, 10:1 to 1:10, 5:1 to 1:5, 2:1 to 1:2, and 1:1.

The optimum ratios, individual and combined dosages, and concentrations of the drug compounds that yield efficacy without toxicity are based on the kinetics of the active ingredients' availability to target sites, and are determined using methods known to those of skill in the art.

The invention being thus described, it will be obvious that the same can be varied in many ways. Such variations are not to be regarded as a departure from the scope of the invention, and all such modifications are intended to be included within the scope of the following claims. For example, any of the specific JAK inhibitors disclosed herein can be combined with any of the PI3K/mTOR inhibitors disclosed herein, and can be used to treat any of the disease states disclosed herein. Furthermore, when the JAK inhibitor and PI3 KmTOR inhibitor are combined into a single dosage form, they can be combined with any pharmaceutically acceptable carrier or carriers described herein.

EXAMPLES

The following examples serve to illustrate the invention without limiting the invention in its scope.

Synthesis of 2-methyl-2-(4-(3-methyl-2-oxo-8-(quinolin-3-yl)-2,3-dihydro-imidazo[4,5-c]quinolin-1-yl)phenyl)propionitrile (Compound A)

Temperatures are measured in degrees celsius (° C.). Unless otherwise indicated, the reactions take place at room temperature (RT). Ratios of solvents (e.g. in eluents or solvent mixtures) are given in volume by volume (v/v).

HPLC linear gradient between A=H$_2$O/TFA 1000:1 and B=acetonitrile/TFA 1000:1; Grad 1: 2-100% B in 4.5 min and 1 min at 100% B; column: Chromolith Performance 100 mm×4.5 mm (Merck, Darmstadt, Germany); flow rate 2 ml/min. Detection at 215 nM; Grad 2: 2-100% B in 5 minutes and 2 minutes at 100% B; column: Nucleosil C$_{18}$ reverse phase; 150 mm×46 mm (SMT, Burkard Instruments, Dietikon, Switzerland); flow rate: 2.0 ml/min Detection at 215 nm.

Example 1a

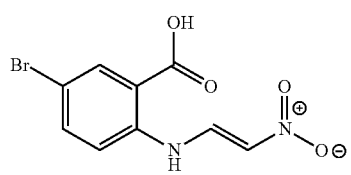 [SMILES: O=C(O)c1cc(Br)ccc1N/C=C/[N+](=O)[O-]]

5-Bromo-2-(2-nitro-vinylamino)-benzoic acid

A suspension of 25 g (16 mmol) of 2-amino-5-bromo-benzoic acid (Fluka, Buchs, Switzerland) in H$_2$O—HCl (37%) (10:1) is stirred for 8 h and then filtered (solution A). 8.17 g (255 mmol) of nitromethane (Fluka, Buchs, Switzerland) are added over 10 min to an ice-bath cooled mixture of 35 g of ice and 15.3 g (382 mmol) of NaOH. After stirring for 1 h at 0° C. and 1 h at rt, the solution is added at 0° C. to 28 g of ice and 42 ml of HCl (37%) (solution B). Solutions A and B are combined and the reaction mixture is stirred for 18 h at RT. The yellow precipitate is filtered off, washed with H$_2$O and dried in vacuo at 40° C. to give the title compound. ES-MS: 287, 289 (M+H)$^+$, Br pattern; $^1$H NMR (DMSO-d$_6$): δ 13.7-14.6/br s (1H), 12.94/d (1H), 8.07/d (1H), 8.03/dd (1H), 7.83/dd (1H), 7.71/d (1H)$_1$ 6.76/d (1H).

Example 1b

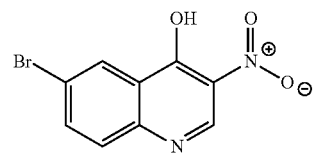 [SMILES: O=[N+]([O-])c1cnc2ccc(Br)cc2c1O]

6-Bromo-3-nitro-quinolin-4-ol 29 g (101 mmol) of 5-bromo-2-(2-nitro-vinylamino)-benzoic acid (Example 1a) and 11.9 g (121 mmol) of potassium acetate in 129 ml (152 mmol) of acetic anhydride are stirred for 1.5 h at 120° C. The precipitate is filtered off and washed with acetic acid until the filtrate is colorless, then is washed with H$_2$O and dried in vacuo to give the title compound. ES-MS: 269, 271 (M+H)$^+$, Br pattern; analytical HPLC: W=2.70 min (Grad 1).

Example 1c

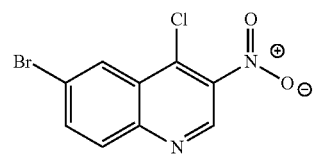

6-Bromo-4-chloro-3-nitro-quinoline 20 g (74.3 mmol) of 6-bromo-3-nitro-quinolin-4-ol (Example 1b) in 150 ml (1.63 mol) of POCl$_3$ are stirred for 45 min at 120° C. The mixture is cooled to RT and poured slowly into ice-water. The precipitate is filtered off, washed with ice-cold water, and dissolved in CH$_2$Cl$_2$. The organic phase is washed with cold brine, and the aqueous phase is discarded. After drying over MgSO$_4$, the organic solvent is evaporated to dryness to provide the title compound. $^1$H NMR (CDCl$_3$): δ 9.20/s (1H), 8.54/d (1H), 8.04/d (1H), 7.96/dd (1H); analytical HPLC: W=4.32 min (Grad 1).

Example 1d

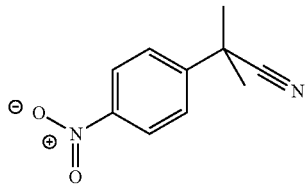

2-Methyl-2-(4-nitro-phenyl)-propionitrile

To 15 g (92.5 mmol) of (4-nitro-phenyl)-acetonitrile (Fluka, Buchs, Switzerland), 1.64 mg (5.09 mmol) of tetrabutylammonium bromide (Fluka, Buchs, Switzerland) and 43.3 g (305 mmol) of iodomethane in 125 mL of $CH_2Cl_2$ are added 10 g (250 mmol) of NaOH in 125 ml of water. The reaction mixture is stirred for 20 h at RT. After this time, the organic layer is separated, dried over $MgSO_4$, and evaporated to dryness. The residue is dissolved in diethyl ether and treated with black charcoal for 30 min., filtered over Celite and evaporated in vacuo to give the title compound as a pale yellow solid. Analytical HPLC: $t_{ret}$=3.60 minutes (Grad 1).

Example 1e

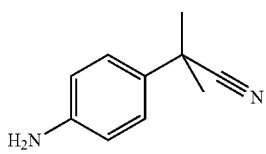

(2-(4-Amino-phenyl)-2-methyl-propionitrile 16 g (84.1 mmol) of 2-methyl-2-(4-nitro-phenyl)-propionitrile (Example 1d) and 4.16 g of Raney-Ni are shacked in 160 ml of THF-MeOH (1:1) under 1.1 bar of $H_2$ for 12 h. at RT. After completion of the reaction, the catalyst is filtered-off and the filtrate is evaporated to dryness. The residue is purified by flash chromatography on silica gel (hexane-EtOAc 3:1 to 1:2) to provide the title compound as an oil. ES-MS: 161 $(M+H)^+$; analytical HPLC: $t_{ret}$=2.13 minutes (Grad 1).

Example 1f

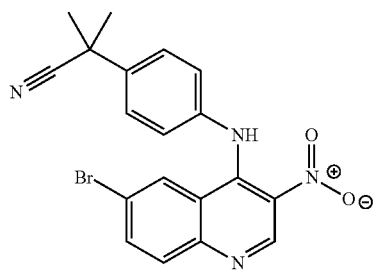 [SMILES: CC(C)(C#N)c1ccc(Nc2c([N+](=O)[O-])cnc3ccc(Br)cc23)cc1]

2-[4-(6-Bromo-3-nitro-quinolin-4-ylamino)-phenyl]-2-methyl-propionitrile 18 g (62.6 mmol) of 6-bromo-4-chloro-3-nitro-quinoline (Example 1c) and 11 g (68.9 mmol) of (2-(4-amino-phenyl)-2-methyl-propionitrile (Example 1e) are dissolved in 350 ml of acetic acid and stirred for 2 h. After this time, water is added and the yellow precipitate is filtered off and washed with $H_2O$. The solid is dissolved in EtOAc-THF (1:1), washed with sat. aqueous $NaHCO_3$ and dried over $MgSO_4$. The organic phase is evaporated to dryness to give the title compound as a yellow solid. ES-MS: 411, 413 $(M+H)^+$, Br pattern; analytical HPLC: $t_{ret}$=3.69 min (Grad 1).

Example 1g

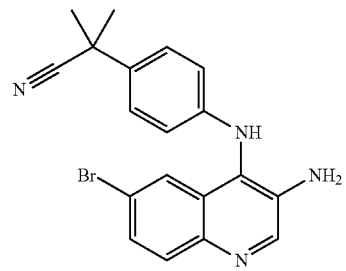 [SMILES: CC(C)(C#N)c1ccc(Nc2c(N)cnc3ccc(Br)cc23)cc1]

2-[4-(3-Amino-6-bromo-quinolin-4-ylamino)-phenyl]-2-methyl-propionitrile 24 g (58.4 mmol) of 2-[4-(6-bromo-3-nitro-quinolin-4-ylamino)-phenyl]-2-methyl-propionitrile (Example 1e) is shacked in 300 ml of MeOH-THE (1:1) under 1.1 bar of $H_2$ in the presence of 8.35 g of Raney-Ni for 1 h. After completion of the reaction, the catalyst is filtered off and the filtrate is evaporated to dryness to give the title compound as a yellow foam. ES-MS: 381, 383 $(M+H)^+$, Br pattern; analytical HPLC: $t_{ret}$=3.21 min (Grad 1).

Example 1h

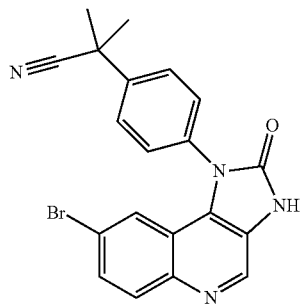 [SMILES: CC(C)(C#N)c1ccc(-n2c(=O)[nH]c3cnc4ccc(Br)cc4c32)cc1]

2-[4-(8-Bromo-2-oxo-2,3-dihydro-imidazo[4,5-c]quinolin-1-yl)-phenyl]-2-methyl-propionitrile A solution of 5 g (13.1 mmol) of 2-[4-(3-amino-6-bromo-quinolin-4-ylamino)-phenyl]-2-methyl-propionitrile (Example 1g) and 1.59 g (15.7 mmol) of triethylamine in 120 ml $CH_2Cl_2$ is added over 40 min to a solution of 2.85 g (14.4 mmol) of trichloromethyl chloroformate (Fluka, Buchs, Switzerland) in 80 ml of CH$_2$Cl$_2$ at 0° C. with an ice-bath. The reaction mixture is stirred for 20 min at this temperature then is quenched with sat. aqueous NaHCO$_3$, stirred for 5 min and extracted with CH$_2$Cl$_2$. The organic layer is dried over Na$_2$SO$_4$, filtered and evaporated in vacuo to give the crude title compound as a brownish solid. ES-MS: 407, 409 (M+H)$^+$, Br pattern; analytical HPLC: t$_{ret}$=3.05 min (Grad 1).

Example 1i

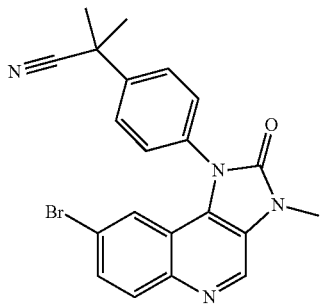 [SMILES: Cn1c(=O)n(-c2ccc(C(C)(C)C#N)cc2)c2c3cc(Br)ccc3ncc21]

2-[4-(8-Bromo-3-methyl-2-oxo-2,3-dihydro-imidazo [4,5-c]quinolin-1-yl)-phenyl]-2-methyl-propionitrile To a solution of 3.45 g (8.47 mmol) of 2-[4-(8-bromo-2-oxo-2,3-dihydro-imidazo[4,5-c]quinolin-1-yl)-phenyl]-2-methyl-propionitrile (Example 1h), 1.8 g (12.7 mmol) of iodomethane (Fluka, Buchs, Switzerland) and 273 mg (0.847 mmol) of tetrabutylammonium bromide (Fluka, Buchs, Switzerland) in 170 ml of CH$_2$Cl$_2$ is added a solution of 508 mg (12.7 mmol) of NaOH (Fluka, Buchs, Switzerland) in 85 ml of H$_2$O. The reaction mixture is stirred for 2 days and 900 mg (6.35 mmol) of iodomethane and 254 mg (6.35 mmol) of NaOH in 5 ml of H$_2$O are added. The reaction mixture is stirred for 1 day at RT. After this time, the reaction is quenched with H$_2$O and extracted with CH$_2$Cl$_2$ (2×). The organic layer is washed with brine, dried over Na$_2$SO$_4$, filtered and evaporated in vacuo to give the title compound as a beige solid. ES-MS: 421, 423 (M+H)$^+$, Br pattern; analytical HPLC: t$_{ret}$=3.15 min (Grad 1).

Example 1j

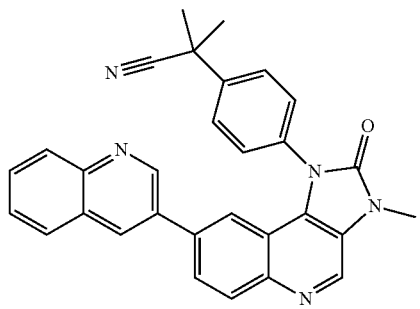 [SMILES: Cn1c(=O)n(-c2ccc(C(C)(C)C#N)cc2)c2c3cc(-c4cnc5ccccc5c4)ccc3ncc21]

2-Methyl-2-(4-(3-methyl-2-oxo-8-(quinolin-3-yl)-2, 3-dihydro-imidazo[4,5-c]quinolin-1-yl)phenyl)propionitrile 0.3 mmol of 3-quinoline boronic acid (Aldrich, Buchs, Switzerland), 8 mg of bis(triphenylphosphine)palladium (II) dichloride (Fluka, Buchs, Switzerland) and 0.5 ml of a 1 M solution of Na$_2$CO$_3$ are added to a solution of 84 mg (0.2 mmol) of 2-[4-(8-bromo-3-methyl-2-oxo-2,3-dihydro-imidazo[4,5-c]quinolin-1-yl)-phenyl]-2-methyl-propionitrile (Example 1i) in 2 ml of DMF. The mixture is stirred for 1 h. at 100° C. After this time, the mixture is quenched with sat. aqueous NaHCO$_3$ and extracted with EtOAc (2×). The organic layer is washed with brine, dried over Na$_2$SO$_4$, filtered and evaporated in vacuo. The residue is loaded on silica gel and purified by flash chromatography to give the title compound. ES-MS: 470 (M+H)$^+$; analytical HPLC: t$_{ret}$=2.90 min (Grad 1).

Synthesis of (3R)- and (3S)-3-cyclopentyl-3-[4-(7H-pyrrolo[2,3-d]pyrimidin-4-yl)-1H-pyrazol-1-yl]propanenitrile (Compound B)

Step 1. (2E)- and (2Z)-3-Cyclopentylacrylonitrile

To a solution of 1.0 M potassium tert-butoxide in THF (235 mL) at 0° C. was added dropwise a solution of diethyl cyanomethylphosphonate (39.9 mL, 0.246 mol) in THF (300 mL). The cold bath was removed and the reaction was warmed to room temperature followed by recooling to 0° C., at which time a solution of cyclopentanecarbaldehyde (22.0 g, 0.224 mol) in THF (60 mL) was added dropwise. The bath was removed and the reaction warmed to ambient temperature and stirred for 64 hours. The mixture was partitioned between diethyl ether and water, the aqueous phase was extracted with three portions of ether, followed by two portions of ethyl acetate. The combined extracts were washed with brine, then dried over sodium sulfate, filtered and concentrated in vacuo to afford a mixture containing 24.4 g of olefin isomers which was used without further purification (89%).

$^1$H NMR (400 MHz, CDCl$_3$): δ 6.69 (dd, 1H, trans olefin), 6.37 (t, 1H, cis olefin), 5.29 (dd, 1H, trans olefin), 5.20 (d, 1H, cis olefin), 3.07-2.95 (m, 1H, cis product), 2.64-2.52 (m, 1H, trans product), 1.98-1.26 (m, 16H).

Step 2. (3R)- and (3S)-3-Cyclopentyl-3-[4-(7-[2-(trimethylsilyl)ethoxy]methyl-7H-pyrrolo[2,-3-d]-pyrimidin-4-yl)-1H-pyrazol-1-yl]propanenitrile To a solution of 4-(1H-pyrazol-4-yl)-7-[2-(trimethylsilyl) ethoxy]methyl-7H-pyrrolo[2,3-d]-pyrimidine (15.0 g, 0.0476 mol) in ACN (300 mL) was added 3-cyclopentylacrylonitrile (15 g, 0.12 mol) (as a mixture of cis and trans isomers), followed by DBU (15 mL, 0.10 mol). The resulting mixture was stirred at room temperature overnight. The ACN was evaporated. The mixture was diluted with ethyl acetate, and the solution was washed with 1.0 N HCl. The aqueous layer was back-extracted with three portions of ethyl acetate. The combined organic extracts were washed with brine, dried over sodium sulfate, filtered and concentrated. The crude product was purified by silica gel chromatography (gradient of ethyl acetate/hexanes) to yield a viscous clear syrup, which was dissolved in ethanol and evaporated several times to remove ethyl acetate, to afford 19.4 g of racemic adduct (93%). The enantiomers were separated by preparative-HPLC, (OD-H, 15% ethanol/hexanes) and used separately in the next step to generate their corresponding final product. The final products (see Step 3) stemming from each of the separated enantiomers were found to be active JAK inhibitors; however, the final product stemming from the second peak to elute from the preparative-HPLC was more active than its enantiomer.

$^1$H NMR (300 MHz, CDCl$_3$): δ 8.85 (s, 1H), 8.32 (s, 2H), 7.39 (d, 1H), 6.80 (d, 1H), 5.68 (s, 2H), 4.26 (dt, 1H), 3.54 (t,

2H), 3.14 (dd, 1H), 2.95 (dd, 1H), 2.67-2.50 (m, 1H), 2.03-1.88 (m, 1H), 1.80-1.15 (m, 7H), 0.92 (t, 2H), −0.06 (s, 9H); MS (ES): 437 (M+1).

Step 3.

To a solution of 3-cyclopentyl-3-[4-(7-[2-(trimethylsilyl) ethoxy]methyl-7H-pyrrolo[2,3-d]-pyrimidin-4-yl)-1H-pyrazol-1-yl]propanenitrile (6.5 g, 0.015 mol, R or S enantiomer as isolated above) in DCM (40 mL) was added TFA (16 mL) and this was stirred for 6 hours. The solvent and TFA were removed in vacuo. The residue was dissolved in DCM and concentrated using a rotary evaporator two further times to remove as much TFA as possible. Following this, the residue was stirred with ethylenediamine (4 mL, 0.06 mol) in methanol (30 mL) overnight. The solvent was removed in vacuo, water was added and the product was extracted into three portions of ethyl acetate. The combined extracts were washed with brine, dried over sodium sulfate, decanted and concentrated to afford the crude product which was purified by flash column chromatography (eluting with a gradient of methanol/DCM). The resulting mixture was further purified by preparative-HPLC/MS (C18 eluting with a gradient of ACN/$H_2O$ containing 0.15% $NH_4OH$) to afford product (2.68 g, 58%).

$^1$H NMR (400 MHz, DMSO-$d_6$): δ 12.11 (br s, 1H), 8.80 (s, 1H), 8.67 (s, 1H), 8.37 (s, 1H), 7.60 (d, 1H), 6.98 (d, 1H), 4.53 (dt, 1H), 3.27 (dd, 1H), 3.19 (dd, 1H), 2.48-2.36 (m, 1H), 1.86-1.76 (m, 1H), 1.68-1.13 (m, 7H); MS(ES): 307 (M+1).

Synthesis of (3R)-3-cyclopentyl-3-[4-(7H-pyrrolo[2,3-d]pyrimidin-4-yl)-1H-pyrazol-1-yl]propanenitrile maleic acid salt To a test tube was added (3R)-3-Cyclopentyl-3-[4-(7H-pyrrolo[2,3-d]pyrimidin-4-yl)-1H-pyrazol-1-yl]propanenitrile (153.7 mg, 0.5 mmol) and maleic acid (61.7 mg) followed by isopropyl alcohol (IPA) (4 mL). The resulting mixture was heated to clear, cooled to room temperature, and then stirred for another 2.5 hours. The precipitate was collected by filtration and the cake was washed with 0.8 mL of cold IPA. The cake was dried under vacuum to constant weight to provide the final salt product (173 mg).

Synthesis of (3R)-3-cyclopentyl-3-[4-(7H-pyrrolo[2,3-d]pyrimidin-4-yl)-1H-pyrazol-1-yl]propanenitrile phosphoric acid salt To a test tube was added (3R)-3-Cyclopentyl-3-[4-(7H-pyrrolo[2,3-d]pyrimidin-4-yl)-1H-pyrazol-1-yl]propanenitrile (153.5 mg) and phosphoric acid (56.6 mg) followed by isopropyl alcohol (IPA) (5.75 mL). The resulting mixture was heated to clear, cooled to room temperature, and then stirred for another 2 hours. The precipitate was collected by filtration and the cake was washed with 0.6 mL of cold IPA. The cake was dried under vacuum to constant weight to provide the final salt product (171.7 mg).

Synthesis of (3R)-3-cyclopentyl-3-[4-(7H-pyrrolo[2,3-d]pyrimidin-4-yl)-1H-pyrazol-1-yl]propanenitrile sulfuric acid salt To a test tube was added (3R)-3-Cyclopentyl-3-[4-(7H-pyrrolo[2,3-d]pyrimidin-4-yl)-1H-pyrazol-1-yl]propanenitrile (153.0 mg) and sulfuric acid (56.1 mg) followed by acetonitrile (7.0 mL). The resulting mixture was heated to clear, cooled to room temperature, and then stirred for another 2 hours. The precipitate was collected by filtration and the cake was washed with 0.8 mL of cold acetonitrile. The cake was dried under vacuum to constant weight to provide the final salt product (180 mg).

Biological Activity

Disregulated JAK/STAT signaling, occurring mainly but not exclusively in cells harboring mutations in JAK2 or other proteins involved in JAK/STAT pathway such as MPL, CBL, or Lnk, represents a pathogenetic event in chronic myeloproliferative neoplasms (MPN). However, activation of other downstream pathways such as the ERK and PI3K/Akt/mTOR pathway has been also documented in JAK2V617F-mutated cells. This study explored in vitro the potential relevance of targeting PI3K/Akt/mTor pathway with specific inhibitors, alone or in combination with JAK2 inhibitor. Indeed, clinical trials have recently documented the effectiveness of JAK1/2 inhibitors (Verstovsek S, *NEJM*, 2010; 363:117; Pardanani A, *JCO* 2011; 29:789; Harrison C, *NEJM* 2012; 366:787; Verstovsek S, *NEJM* 2012; 366:799) and RAD001, an mTOR inhibitor (Guglielmelli S, *Blood* 2011; 118:2069), in patients with myelofibrosis.

The following drugs were used: an allosteric (RAD001) and an ATP (PP242) mTOR competitor; a dual PI3K/mTOR inhibitor 2-methyl-2-[4-(3-methyl-2-oxo-8-quinolin-3-yl-2,3-dihydro-imidazo[4,5-c]quinolin-1-yl)-phenyl]-propionitrile (Compound A); a JAK1/2 kinase ATP competitor (3R)-3-cyclopentyl-3-[4-(7H-pyrrolo[2,3-d]pyrimidin-4-yl)-1H-pyrazol-1-yl]propanenitrile (Compound B).

In vitro Data.

Mouse (Ba/F3 and Ba/F3-EPOR wild-type or expressing JAK2V617F(VF)) and human (JAK2VF mutated HEL and SET2) cell lines and primary MPN CD34+ cells from patients with myelofibrosis (MF) or polycythemia vera (PV) were used; BCR/ABL mutated K562 cells were used in some experiments. Cell proliferation, colony formation, apoptosis, cell cycle and protein phosphorylation status were evaluated. Effects of drug combination were analyzed according to Chou and Talalay to calculate the combination index (CI); a CI<1.0 indicates synergistic activity.

In the Ba/F3-EPOR JAK2V617F-mutated cells, cell proliferation was prevented by lower doses of RAD001 (615±50 nM, measured as IC50), PP242 (98±5 nM) and Compound A (87±50 nM) compared to Ba/F3-EPOR JAK2 wild-type (wt) cells (>10,000 nM; 5,931±1,000 nM; 676±200 nM, respectively). In the case of the JAK inhibitor, the IC50 was 51±2 nM for Compound B as compared to 457±15 nM in wild-type cells. All above drugs were able to prevent short-term cell proliferation and colony formation in JAK2V617F-mutated HEL and SET2 cells as well. In particular, Compound A induced preferential inhibition in HEL and SET2 cells compared to K562 cells (IC50, 387±90 nM and 334±40 nM vs 5,000±1,000 nM; P<0.01).

mTOR inhibitors induced cell cycle arrest in Go but were very poor inducers of apoptosis (less than 15-20% at maximum); conversely JAK1/2 inhibitors induced dose-dependent increase of Annexin-V +ve cells up to >60% and Compound A induced 30-40% apoptosis at highest concentrations. Western blot analysis demonstrated that, in addition to the expected inhibition of phosphorylation of specific drug targets (mTOR, 4EBP1), all three PI3K/mTOR inhibitors also reduced the degree of phophoSTAT5. siRNA-induced down-regulation of mTOR in SET2, HEL and Ba/F3-EPOR JAK2V617F cells resulted in reduced phosphoSTAT5, indicating a direct mTOR-dependent phopshoSTAT5 regulation.

Then, the activity of RAD001 and Compound A was analyzed in primary cells from MPN patients. Both drugs reduced clonogenic growth of MPN erythroid, myeloid and megakaryocytic progenitors at doses significantly lower (from 5 to 10-fold) than in normal cells, and prevented erythropoietin-independent colony (EEC) formation in the low nM range. In particular, Compound A impaired the proliferation of CD34+ cells of MF pts with an IC50=43±20 vs 780±150 in healthy donors (P<0.01), and reduced colony formation of MF and PV hematopoietic progenitors at statistically lower doses (2 to 15-fold) compared to normal cells; the growth of EPO-independent colonies (EEC) of PV patients cells was potently inhibited (IC50=20±10 nM). Single-colony genotyping in JAK2V617F mutated patients cells showed a 40±16% reduction of VF in favor of wild-type colonies (range 18-71%, n=7). Overall, these data indicated that inhibitors of PI3K/mTOR prevent proliferation and clonogenic capacity of MPN cells mainly through a cytostatic rather apoptotic effect (as JAK1/2 inhibitors preferentially do).

To determine whether simultaneous treatment with PI3K/AKt and JAK1/2 inhibitor displayed synergism, SET2 cells were treated with different drug doses and their proliferation and apoptotic rate were measured. Synergism was calculated as the combination index (CI) according to Chou and Talalay. Evidence of synergism was obtained for Compound B with RAD001 (CI: 0.20), PP242 (CI: 0.20) and Compound A (CI: 0.37). Co-treatment of Compound A plus Compound B resulted in a synergistic increase of the apoptosis rate in SET2 (CI=0.25).

Synergism was similarly demonstrated in Ba/F3-EPOR JAK2V617F-mutated cells. Co-treatment of Compound A plus Compound B resulted in synergistic inhibition of proliferation in BaF3-EPOR VF (CI=0.77) cells. Activity of RAD001 with Compound B was also assessed in an EEC assay. It was found that addition of RAD001 (5 nM) or Compound A (50 nM) to very low doses of JAK1/2 inhibitors (in the range of 5 to 50 nM) resulted in significant synergism and almost completely prevented EEC formation. In particular, the combination of Compound A and Compound B was highly effective in the EEC assay with a CI=0.17±0.04.

In summary, these in vitro data indicate that PI3K/mTOR inhibitors are active against MPN cells and their combination with JAK1/2 inhibitors produced synergism, allowing the use of lower doses of each drug. Thus, concurrent targeting of PI3K/mTOR and JAK/STAT pathway might represent a new therapeutic strategy to optimize efficacy and reduce toxicity in patients with MPN.

In Vivo Data:
I.

To ascertain the effects of drugs targeting PI3K/Akt/mTOR pathway alone and in combination with JAK2 inhibitor in a murine model of myeloproliferative neoplasms, a SCID BaF3 JAK2$^{V617F}$-luciferase mouse model was used. This allows the monitoring of leukemic clone spread by the monitoring of luciferase activity, at the same time providing estimates of mice survival since it does not require killing of the animals to establish the progression and extent of disease. Female SCID mice (4-6 weeks of age; Harlan) were fed rodent standard chow and provided with water ad libitum. Mice were given $3\times10^6$ JAK2$^{V617F}$-luc+ cells by tail vein injection. Mice were injected with D-luciferin before imaging to detect a bioluminescence signal that is proportional to the clone burden. Baseline imaging was performed using a Photon Imager (Biospace Lab) apparatus to establish bioluminescence on day 6 after cell injection. Then, mice were randomly divided into treatment cohorts of six mice each (Vehicle, Compound A, Compound B, Compound A plus Compound B). Drugs treatment was administered daily per os (by mouth). Imaging was performed on day 7, 14, 21, and 28 after the first drug dose. Mice were followed daily for survival and humanely sacrificed when they developed hind limb paralysis or became moribund and considered deceased at the time at which they were sacrificed.

Mice received the following treatments (Table 1): Vehicle only, 60 mpk Compound B, 45 mpk Compound A, and 60 mpk Compound B plus 45 mpk Compound A. Animals did not show appreciable body weight loss. Mean lifespan of Compound A plus Compound B cotreated mice was significantly increased compared to control mice (+54%, p<0.01), Compound B treated (+35.2%, p<0.02) and Compound A treated (+11.9%) showing a synergistic effect against BaF3 JAK$^{V617F}$ cells (See Table 1). In vivo imaging showed a delay of proliferation of BaF3-luc+ cells in mice receiving combination therapy as compared to all other treatment cohorts. In mice receiving the combination therapy, an intense bioluminescent signal was not recorded before day 28 following the administration of the first drug dose as compared to progressive increases in the other experimental groups.

TABLE 1

Mean lifespan of treatment groups.

| TREATMENT | MEAN LIFESPAN (DAYS) | LIFESPAN INCREASE (%) VS VEHICLE | P VALUE VS VEHICLE |
|---|---|---|---|
| Vehicle | 16 | / | / |
| 60 mpk Compound B | 19 | 19% | n.s. |
| 45 mpk Compound A | 24 | 42% | p < .02 |
| 60 mpk Compound B plus 45 mpk Compound A | 29.5 | 54% | p < .01 |

II.

A C57B16/J JAK2 V617F Knock-in (KI) mouse model was generated by the flex switch strategy with insertion of inactivated V617F exon 13 sequence; mating with Vav-Cre mouse activates the VF allele producing a MPN phenotype in the progeny that results JAK2VF heterozygous. Mice were treated for 5 days, then blood, spleen and bone marrow cells were obtained for further analysis.

In KI mice treated for 5 days, drug combination was significantly more effective in reducing spleen weight (median spleen index (calculated as the ratio of spleen weight to body weight×100): 38, 35, 27 and 7 for Vehicle, Compound A, Compound B, and Compound A plus Compound B, respectively) and reticulocyte count median (No. per HPF (high-power field): 48, 50, 44, 35 and 3 for Vehicle, Compound A, Compound B, and Compound A plus Compound B, respectively) than either drugs alone. The phosphorylation levels of STAT5 and 4EBP1 in the spleen was significantly reduced in mice receiving Compound A plus Compound B as compared to single treatment with either Compound A or Compound B.

The invention claimed is:

1. A method of treating primary or idiopathic myelofibrosis, essential thrombocythemia, or polycythemia vera in a subject in need thereof comprising: administering to the subject an effective amount of a combination therapy comprising (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, and 2-methyl-2-[4-(3-methyl-2-oxo-8-quinolin-3-yl-2,3-dihydro-imidazo[4,5-c]quinolin-1-yl)-phenyl]-propionitrile, or a pharmaceutically acceptable salt thereof, wherein the ratio of 2-methyl-2-[4-(3-methyl-2-oxo-8-quinolin-3-yl-2,3-dihydro-imidazo[4,5-c]quinolin-1-yl)-phenyl]-propionitrile to (3R)-3-cyclopentyl-3-[4-(7H-pyrrolo[2,3-d]pyrimidin-4-yl)-1H-pyrazol-1-yl]propanenitrile is from about 3:4 to about 10:1.

2. The method of claim 1, wherein the subject is human.

3. The method of claim 1, wherein the compound (3R)-3-cyclopentyl-3-[4-(7H-pyrrolo[2,3-d]pyrimidin-4-yl)-1H-pyrazol-1-yl]propanenitrile is (3R)-3-cyclopentyl-3-[4-(7H-pyrrolo[2,3-d]pyrimidin-4-yl)-1H-pyrazol-1-yl] propanenitrile phosphoric acid salt.

4. The method of claim 1, wherein (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, and 2-methyl-2-[4-(3-methyl-2-oxo-8-quinolin-3-yl-2,3-dihydro-imidazo[4,5-c]quinolin-1-yl)-pheny]propionitrile, or a pharmaceutically acceptable salt thereof, are in a single formulation or unit dosage form.

5. The method of claim 1, wherein (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, and 2-methyl-2-[4-(3-methyl-2-oko-8-quinolin-3-yl-2,3-dihydro-imidazo[4,5-c]quinolin-1-yl)-phenyl]-propionitrile, or a pharmaceutically acceptable salt thereof, are in separate formulitions or unit dosage forms.

6. The method of claim 1, wherein the treatment comprises administering (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, and 2-methyl-2-[4-(3-methyl-2-oxo-8-quinolin-3-yl-2,3-dihydro-imidazo[4,5-c]quinolin-1-yl)-phenyl]propionitrile, or a pharmaceutically acceptable salt thereof, at substantially the same time.

7. The method of claim 1, wherein (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, is administered to the subject, followed by administration of 2-methyl-2-[4-(3-methyl-2-oxo-8-quinolin-3-yl-2,3-dihydro-imidazo[4,5-c]quinolin-1-yl)-phenyl]-propionitrile, or a pharmaceutically acceptable salt thereof.

8. The method of claim 1, wherein 2-methyl-2-[4-(3-methyl-2-oxo-8-quinolin-3-yl-2,3-dihydro-imidazo[4,5-c]quinolin-1-yl)-phenyl]-propionitrile, or a pharmaceutically acceptable salt thereof, is administered to the subject, followed by administration of (3R)-3-cyclopentyl-3-[4-(7H-pyrrolo[2,3-d]pyrimidin-4-yl)-1H-pyrazol-1-yl]propanenitrile, or a pharmaceutically acceptable salt thereof.

9. A method of treating primary myelofibrosis in a subject in need thereof comprising administering to the subject an effective amount of a combination therapy comprising (3R)-3-cyclopentyl-3-[4-(7H-pyrrolo[2,3-d]pyrimidin-4-yl)-1H-pyrazol-1-yl]propanenitrile, or a pharmaceutically acceptable salt thereof, and 2-methyl-2-[4-(3-methyl-2-oxo-8-quinolin-3-yl-2,3-dihydro-imidazo[4,5-c]quinolin-1-yl)-phenyl]-propionitrile, or a pharmaceutically acceptable salt thereof, wherein the ratio of 2-methyl-2-[4-(3-methyl-2-oxo-8-quinolin-3-yl-2,3-dihydro-imidazo[4,5-c]quinolin-1-yl)-phenyl]-propionitrile to (3R)-3-cyclopentyl-3-[4-(7H-pyrrolo[2,3-d]pyrimidin-4-yl)-1H-pyrazol-1-yl]propanenitrile is from about 3:4 to about 10:1.

* * * * *